US012485271B2

(12) United States Patent
West

(10) Patent No.: US 12,485,271 B2
(45) Date of Patent: Dec. 2, 2025

(54) SYSTEMS AND METHODS FOR MEDICAL DEVICE CONNECTORS

(71) Applicant: TC1 LLC, St. Paul, MN (US)

(72) Inventor: Dustin Seth West, Westford, MA (US)

(73) Assignee: TC1 LLC, St. Paul, MN (US)

( * ) Notice: Subject to any disclaimer, the term of this patent is extended or adjusted under 35 U.S.C. 154(b) by 897 days.

(21) Appl. No.: 17/720,978

(22) Filed: Apr. 14, 2022

(65) Prior Publication Data

US 2022/0331580 A1 Oct. 20, 2022

Related U.S. Application Data

(60) Provisional application No. 63/175,175, filed on Apr. 15, 2021.

(51) Int. Cl.

| | |
|---|---|
| ***A61N 1/375*** | (2006.01) |
| ***A61M 60/178*** | (2021.01) |
| ***A61M 60/871*** | (2021.01) |
| ***A61N 1/378*** | (2006.01) |
| ***H01R 24/58*** | (2011.01) |
| ***H02J 50/10*** | (2016.01) |

(52) U.S. Cl.

CPC ........ *A61M 60/871* (2021.01); *A61M 60/178* (2021.01)

(58) Field of Classification Search

CPC .............. H01R 13/187; H01R 13/5224; H01R 2201/12; H01R 24/58; A61N 1/3752; A61N 1/3787; H02J 50/10; H02J 50/12

See application file for complete search history.

(56) References Cited

U.S. PATENT DOCUMENTS

| | | | |
|---|---|---|---|
| 4,112,953 | A | 9/1978 | Shanker |
| 5,730,628 | A | 3/1998 | Hawkins |

(Continued)

FOREIGN PATENT DOCUMENTS

| | | | |
|---|---|---|---|
| EP | 3093927 | A1 | 11/2016 |
| WO | 2015134871 | A1 | 9/2015 |

(Continued)

OTHER PUBLICATIONS

Extended European Search Report issued in European Patent Application No. 22168633.0, dated Sep. 13, 2022, 15 pages.

*Primary Examiner* — Jon Eric C Morales
(74) *Attorney, Agent, or Firm* — Armstrong Teasdale LLP

(57) ABSTRACT

A connector assembly for use in a medical device system is provided. The connector assembly includes a female connector including a jack and at least one female electrical contact disposed in the jack, where the at least one female electrical contact includes an outer ring and leaf springs extending both radially inward from the outer ring and longitudinally along the jack. The connector assembly also includes a male connector including a plug adapted to be inserted into the jack of the female connector, and at least one male electrical contact disposed on the plug, where the at least one male electrical contact is configured to electrically couple to a corresponding female electrical contact of the at least one female electrical contact by contacting the plurality of leaf springs of the corresponding female electrical contact when the plug of the male connector is inserted into the jack of the female connector.

5 Claims, 10 Drawing Sheets

(56) References Cited

U.S. PATENT DOCUMENTS

| | | | | |
|---|---|---|---|---|
| 10,610,308 | B2 | 4/2020 | Sema | |
| 11,116,542 | B2 | 9/2021 | Jimenez et al. | |
| 2005/0107859 | A1 | 5/2005 | Daglow | |
| 2006/0004419 | A1 | 1/2006 | Olbertz | |
| 2010/0191299 | A1 | 7/2010 | Ayzenberg | |
| 2013/0116754 | A1 | 5/2013 | Sharma | |
| 2016/0058433 | A1 | 3/2016 | Burbank | |
| 2016/0059019 | A1 | 3/2016 | Malinowski | |
| 2016/0367819 | A1 * | 12/2016 | Eldridge ................. | H02J 50/10 |
| 2018/0243488 | A1 | 8/2018 | Callaway et al. | |
| 2018/0264237 | A1 | 9/2018 | Palushi | |
| 2020/0101210 | A1 | 4/2020 | Jimenez et al. | |
| 2021/0085402 | A1 | 3/2021 | Salazar | |

FOREIGN PATENT DOCUMENTS

| | | | |
|---|---|---|---|
| WO | 2016145029 | A1 | 9/2016 |
| WO | 2021005362 | A1 | 1/2021 |
| WO | 2021062429 | A1 | 4/2021 |

* cited by examiner

SYSTEMS AND METHODS FOR MEDICAL DEVICE CONNECTORS

CROSS-REFERENCE TO RELATED APPLICATIONS

This application claims priority to U.S. Provisional Application No. 63/175,175, filed on Apr. 15, 2021, which is hereby incorporated by reference in its entirety.

BACKGROUND OF THE DISCLOSURE a. Field of the Disclosure

The present disclosure relates generally to implantable medical devices, and more specifically, relates to connection systems for use in implantable medical devices.

b. Background

Ventricular assist systems (VASs) may include ventricular assist devices (VADs), such as implantable blood pumps used for both short-term (i.e., days, months) and long-term (i.e., years or a lifetime) applications where a patient's heart is incapable of providing adequate circulation, commonly referred to as heart failure or congestive heart failure. A patient suffering from heart failure may use a VAS while awaiting a heart transplant or as a long-term destination therapy. In another example, a patient may use a VAS while recovering from heart surgery. Thus, a VAS may supplement a weak heart (i.e., partial support) or may effectively replace the natural heart's function. VASs may be implanted in the patient's body and powered by an electrical power source inside or outside the patient's body.

According to the American Heart Association, more than five million Americans are living with heart failure, with about 670,000 new cases diagnosed every year. People with heart failure often have shortness of breath and fatigue. Years of living with blocked arteries or high blood pressure may leave the heart too weak to pump enough blood to the body. As symptoms worsen, advanced heart failure develops.

Operation of a VAD may be controlled and/or affected by a controller communicatively coupled with the VAD. The controller may be an external controller or an implanted controller. The operation of the controller may control all or portions of the operation of the VAD including, for example, a speed of the VAD. Some controllers, for example, may monitor one or more parameters relevant to the patient and may affect operation of the VAD according to those one or more monitored parameters. This may include, for example, changing the VAD speed in response to an increase or decrease in physical activity, or the like. Controllers are typically connected to the VAD via a wired connection. Additionally, some controllers are connected to one or more power sources via a wired connection. It would be desirable to improve the connectors in these wired connections to facilitate ease of use and to improve durability.

SUMMARY OF THE DISCLOSURE

The present disclosure is directed to a connector assembly for use in a medical device system. The connector assembly is configured to communicate power and control signals to a medical device. The connector assembly includes a female connector including a jack and at least one female electrical contact disposed in the jack, where the at least one female electrical contact includes an outer ring and a plurality of leaf springs extending both radially inward from the outer ring and longitudinally along the jack. The connector assembly also includes a male connector including a plug adapted to be inserted into the jack of the female connector, and at least one male electrical contact disposed on the plug, where the at least one male electrical contact is configured to electrically couple to a corresponding female electrical contact of the at least one female electrical contact by contacting the plurality of leaf springs of the corresponding female electrical contact when the plug of the male connector is inserted into the jack of the female connector.

The present disclosure is also directed to a connector assembly for use in a medical device system. The connector assembly is configured to communicate power and control signals to a medical device. The connector assembly includes a female connector including a jack and at least one female electrical contact disposed in the jack, where the at least one female electrical contact includes two circumferentially extending rails, and a plurality of ribs extending between the rails. The connector assembly also includes a male connector including a plug adapted to be inserted into the jack of the female connector, and at least one male electrical contact disposed on the plug, where the at least one male electrical contact is configured to electrically couple to a corresponding female electrical contact of the at least one female electrical contact by contacting the plurality of ribs of the corresponding female electrical contact when the plug of the male connector is inserted into the jack of the female connector.

The present disclosure is further directed to a connector assembly for use in a medical device system. The connector assembly is configured to communicate power and control signals to a medical device. The connector assembly includes a female connector including a jack and at least one female electrical contact disposed in the jack, where the at least one female electrical contact includes a wire mesh coupled to a tube, the wire mesh including a plurality of wires extending along the tube. The connector assembly also includes a male connector including a plug adapted to be inserted into the jack of the female connector, and at least one male electrical contact disposed on the plug, where the at least one male electrical contact is configured to electrically couple to a corresponding female electrical contact of the at least one female electrical contact by contacting the plurality of wires of the corresponding female electrical contact when the plug of the male connector is inserted into the jack of the female connector.

The present disclosure is further directed to a method of manufacturing a female connector for use in a connector assembly. The method includes die cutting a sheet of material, and forming the die cut sheet of material into an outer ring and a plurality of leaf springs to form the female connector, where the female connector is formed by plastically deforming the sheet of material, and where the plurality of leaf springs extend both radially inward from the outer ring and longitudinally along the female connector.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
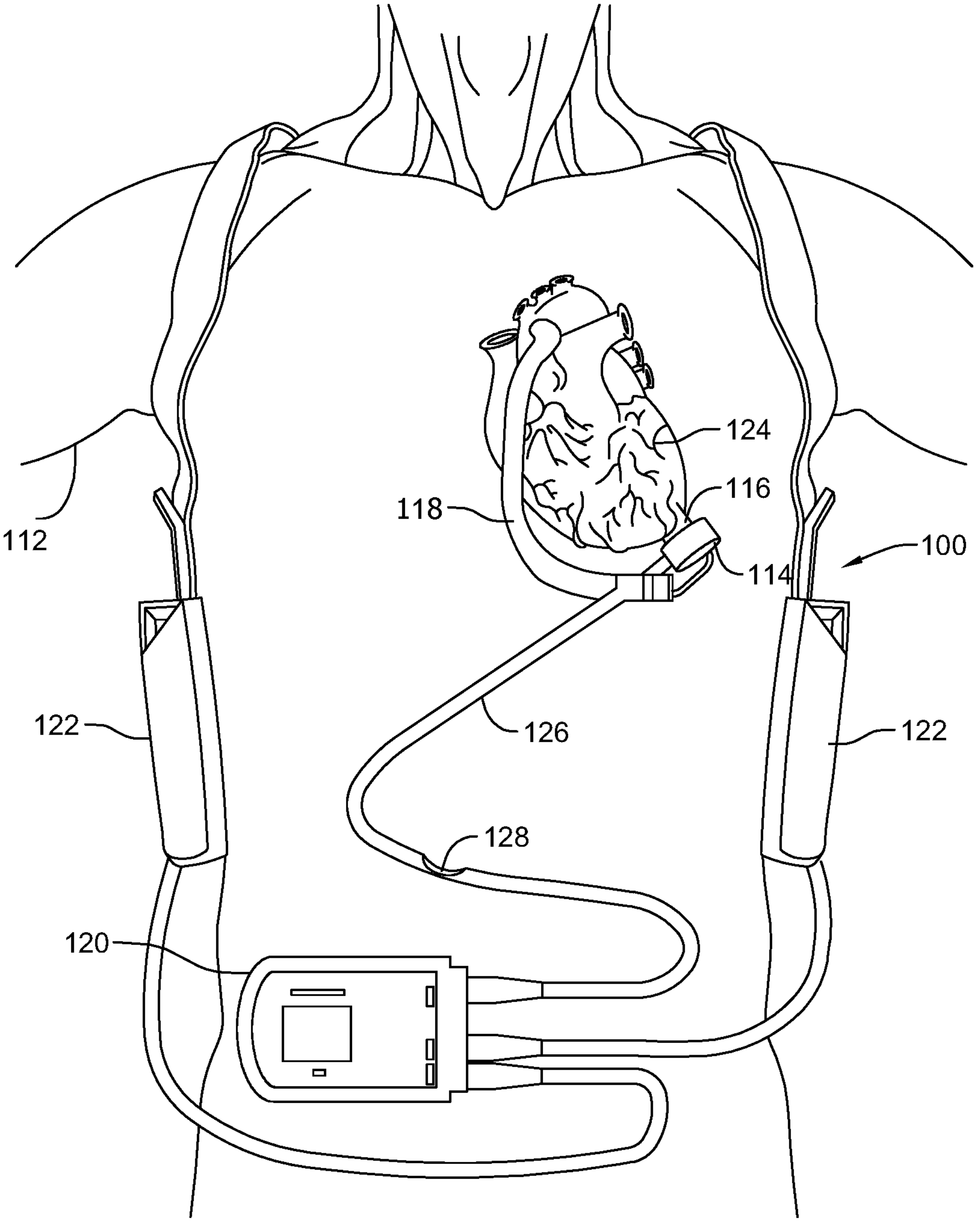
FIG. 1 is a schematic diagram of one embodiment of a mechanical circulatory support system including a wired power system.

The disclosure provides systems and methods for connections in a medical device system. In one embodiment, a connector system (also referred to herein as a "connector assembly") includes a female connector including a jack and at least one female electrical contact disposed in the jack. The at least one female electrical contact includes an outer ring, and a plurality of leaf springs that extend both radially inward from the outer ring and longitudinally along the jack. The connector system also includes a male connector including a plug and at least one male electrical contact. The plug is adapted to be inserted into the jack of the female connector, and the at least one male electrical contact is disposed on the plug. The at least one male electrical contact is configured to electrically couple to a corresponding female electrical contact of the at least one female electrical contact by contacting the plurality of leaf springs of the corresponding female electrical contact when the plug of the male connector is inserted into the jack of the female connector.

Circulatory support systems are increasingly used to support blood circulation in patients. These circulatory systems may include an implantable blood pump, such as a VAD, and a controller. In some embodiments, the controller may directly control the implantable blood pump via one or more control signals, and/or the controller may provide one or more parameters that may be used by the implantable blood pump to affect operation of the implantable blood pump, such as, for example, to change a speed of the implantable blood pump.

Due to this role of the controller in affecting operation of the implantable blood pump, reliability and ruggedness of the controller are important. However, in many instances, controllers are coupled to either a power source such as an external power source or to the implantable blood pump via one or more cables, wires, drivelines, or the like. The connection of the controller with the other components relies on connectors that form this coupling. These connectors may be a weak spot in such circulatory systems because connectors and the contacts that form part of connectors may be exposed to environmental factors that affect the ability of the connectors to reliably function over an extended time period. While numerous improvements have been made to connectors to minimize risk of damage to the connectors and to improve connector reliability, further improvements are desired.

Such improvements may enhance the connector to minimize susceptibility to environmental factors, corrosion, and/or contamination of all or portions of the connector with foreign objects that may hinder coupling. Such improvements may further facilitate connecting the connector and may facilitate aligning the connector insert and the connector receptacle to improve the connection. In some embodiments, for example, a connector may include one or more seals that seal contacts and/or that isolate contacts. In some embodiments, the connector may include one or more features that may facilitate draining the connector of any fluid that may be in the connector at the time of coupling. Further, in some embodiments, the connector may include one or more features that automatically align the connector when coupled and/or that facilitate coupling of the connector.

These features that facilitate alignment may include, for example, the shape of the connector insert and/or the connector receptacle. In some embodiments, for example, the connector insert has a particular shape, and the connector receptacle has a complementary shape that allows insertion of the connector insert in one of a finite number of orientations into the connector receptacle. In some embodiments, the shape may allow insertion of the connector insert into the connector receptacle in multiple orientations (e.g., in two orientations oriented 180° relative to each other). In some embodiments, the contacts in the connector receptacle and the contacts of the connector insert may be arranged to properly mate when the connector insert is inserted into the connector receptacle in any of the finite number of possible orientations.

Referring now to the drawings wherein like reference numerals are used to identify identical components in the various views, FIG. 1 illustrates one example embodiment of a mechanical circulatory support system 100, also referred to herein as an implantable blood pump system 100. Mechanical circulatory support system 100 is partially implanted in a patient's body 112. Mechanical circulatory support system 100 includes an implantable blood pump 114, a ventricular cuff 116, an outflow cannula 118, a system controller 120, and external power sources 122.

Implantable blood pump 114 may include a VAD that is attached to an apex of the left ventricle, as illustrated, or the right ventricle, or both ventricles of a heart 124. The VAD may include a centrifugal (as shown) or axial flow pump that is capable of pumping the entire output delivered to the left ventricle from the pulmonary circulation (i.e., up to 10 liters per minute). Related blood pumps applicable to the present disclosure are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety.

Blood pump 114 may be attached to heart 124 via ventricular cuff 16, which is sewn to heart 124 and coupled to blood pump 114. The other end of blood pump 114 connects to the ascending aorta via outflow cannula 18 so that the VAD effectively diverts blood from the weakened ventricle and propels it to the aorta for circulation to the rest of the patient's vascular system.

In FIG. 1, mechanical circulatory support system 100 is illustrated in a configuration in which powered operation is enabled via external power source 122. A driveline 126, which exits through a patient's abdomen 128, connects implanted blood pump 114 to system controller 120, which monitors operation of system 100. Related controller systems applicable to the present disclosure are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety.

System 100 may be powered by one, two, or more external power sources 122. In some embodiments, one or more energy storage components, such as, for example, one or more batteries, in controller 120 may power mechanical circulatory support system 100. It will be appreciated that although system controller 120 and power source 122 are illustrated as being outside/external to the patient body, driveline 126, system controller 120 and/or power source 122 may be partially or fully implantable within the patient, as separate components or integrated with blood pump 114. In some embodiments, for example, system controller 120 may be implanted within the patient's body, and may receive power from power source 122 that is external to the patient's body. In some embodiments, this power may be provided to controller 120 via a wired or wireless connection between controller 120 and power source 122. In some embodiments, the wireless connection may include a transcutaneous energy transfer system (TETS) that may, for example, include one or more resonant circuits. Examples of such modifications are further described in U.S. Pat. No. 8,562,508 and U.S. Patent Publication No. 2013/0127253, all of which are incorporated herein by reference for all purposes in their entirety.

Figure 2:
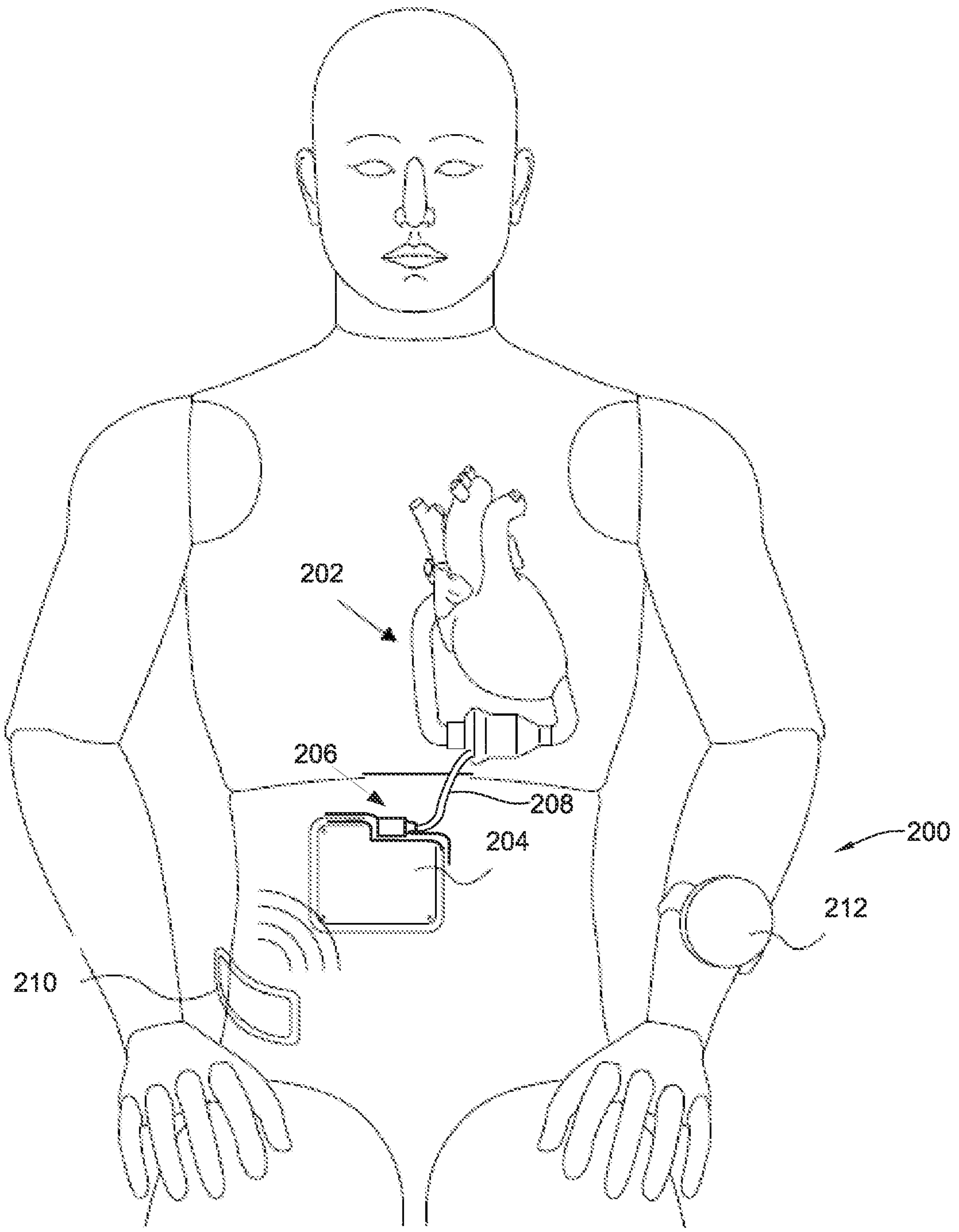
FIG. 2 is a schematic diagram of one embodiment of a mechanical circulatory support system including a wireless power system.

FIG. 2 is a schematic drawing of one embodiment of a mechanical circulatory support system 200. System 200 includes an implanted medical device 202 (shown as a ventricular assist device) and an implanted module 204 configured to receive wireless power from outside the body to provide power and control signals for implanted medical device 202. System 200 may perform similar functions as system 100, shown in FIG. 1. A bulkhead connector 206 and driveline cable 208 connect implanted module 204 to implanted medical device 202 to provide power, data, and or/control signals from implanted module 204 to implanted medical device 202. In one embodiment, implanted medical device 202 is a relatively high-powered device. In some embodiments, implanted module 204 supplies average power of about 5 VAC, about 10 VAC, or about 15 VAC. In some embodiments, implanted module 204 supplies peak power of 5 VAC, 10 VAC, 15 VAC, or 25 VAC. In one embodiment, implanted module 204 is configured to remain inside the patient's body for a minimum of three years, and to serve as the power source and controller for implanted medical device 202. In an example embodiment, implanted module 204 is configured to supply ~16 VAC to drive implanted medical device 202. In other embodiments, an external controller may be in communication with implanted module 204. In these embodiments, the external controller may include an electronic computing device such as a personal computer, a tablet, smartphone, or laptop computer.

In another embodiment, implanted module 204 may include a receiver resonator coil and electronics configured to receive wireless energy from an external transmitter 210, which may include a power supply such as a pulse generator connected to a transmitter resonator coil. Bulkhead connector 206 may allow a clinician to surgically replace implanted module 204 by disconnecting driveline cable 208 from implanted module 204, removing implanted module 204, and reconnecting driveline cable 208 to a new module without removing implanted medical device 202. Similarly, the clinician may surgically replace driveline cable 208 and/or implanted medical device 202 while leaving implanted module 204 in place. In some embodiments, an external user interface 212 may be configured to communicate with implanted module 204 and may be worn by the patient, such as on the patient's wrist. In other embodiments, external user interface 212 may be included in an electronic computing device such as a personal computer, a tablet, smartphone, or laptop computer.

Figure 3:
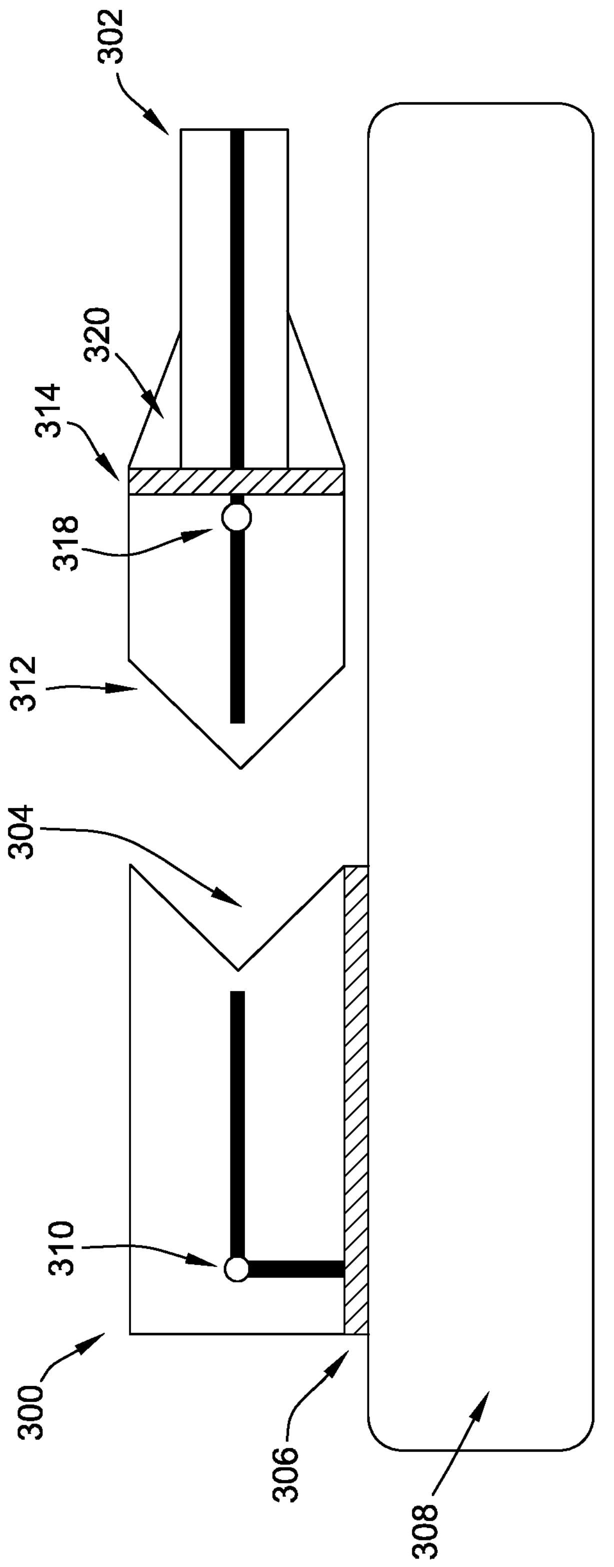
FIG. 3 is a schematic drawing of a bulkhead connector that may be used with the systems shown in FIGS. 1 and 2.

FIG. 3 shows an interface between a bulkhead connector 300, such as bulkhead connector 206 (shown in FIG. 2) and a driveline cable 302, such as driveline cable 208 (shown in FIG. 2) that may be used, for example, with systems 100 and 200 shown in FIGS. 1 and 2. Bulkhead connector 300 includes a female connector 304, a mechanical interface 306 connecting female connector 304 to an implanted module 308, such as implanted module 204 (shown in FIG. 2), and an electrical interface 310. Driveline cable 302 includes a male connector 312, a mechanical interface 314, an electrical interface 318, and a strain relief 320 on driveline cable 302 at an end of male connector 312. Mechanical interface 306 between female connector 304 and implanted module 308, and mechanical interface 314 between male connector 312 and driveline cable 302 may each include an adhesive, for example, an epoxy. It should be understood that in other embodiments, bulkhead connector 300 may include male connector 312 and driveline cable 302 may include female connector 304.

Various aspects of the bulkhead connector are similar to those shown and described in U.S. Pat. Nos. 4,655,462, 4,826,144, 4,876,781, 4,907,788, 4,915,366, 4,961,253, 4,964,204, 5,139,243, 5,160,122, 5,503,375, 5,615,870, 5,709,371, 5,791,638, 7,055,812, 4,678,210, 5,082,390, 5,411,348, 5,545,842, 6,749,358, 6,835,084, 7,070,455, and 7,195,523, the entire contents of which are incorporated herein for all purposes by reference.

Figure 4A:
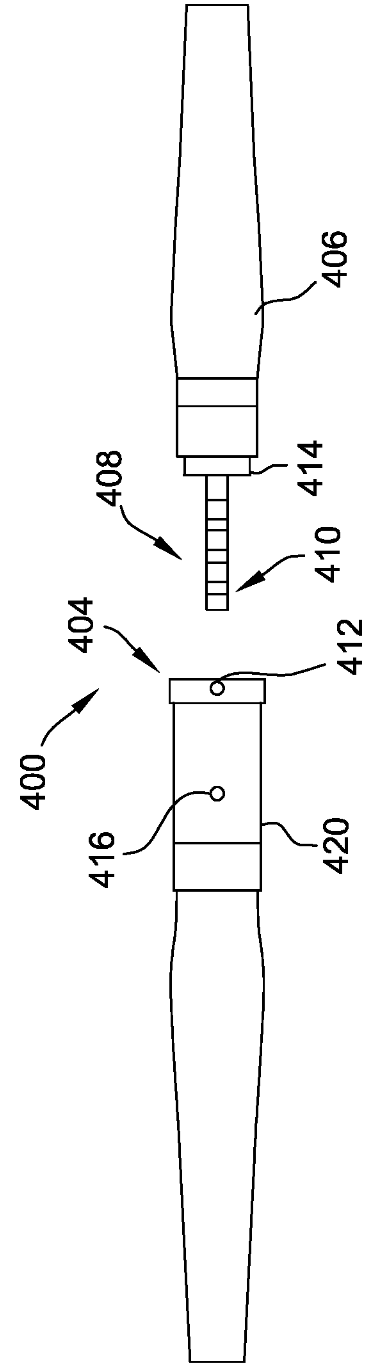
FIGS. 4A-4C illustrate various views of an electrical connector that may be used with the systems shown in FIGS. 1 and 2.

FIG. 4A shows an embodiment of a connector assembly 400 that may be used to implement, for example, the interface between bulkhead connector 300 and driveline cable 302 (shown in FIG. 3). Connector assembly 400 includes a first cable 402 with a female connector 404, such as female connector 304 (shown in FIG. 4) and a second cable 406 with a male connector 408, such as male connector 312 (shown in FIG. 3). As shown, female connector 404 may include a jack (not shown) or slot within which a male plug 410 included in male connector 408 may be inserted to make an electrical connection between female connector 404 and male connector 408. As shown in the embodiment of FIG. 4A, male connector 408 includes a single plug and female connector 404 includes a single jack, but it should be understood that other embodiments may include any suitable number of jacks and plugs. In addition, first cable 402 may include a set locking screw 412, and second cable 406 may include a set screw locking groove 414. In one embodiment, inclusion of a hydrostatic lock between male connector 408 and female connector 404 may be avoided by including a vent 416 in a connector, such as in female connector 404, to release excess fluid or pressure when the connection is made. Vent 416 may include a passive one-way valve, for example.

Figure 4B:
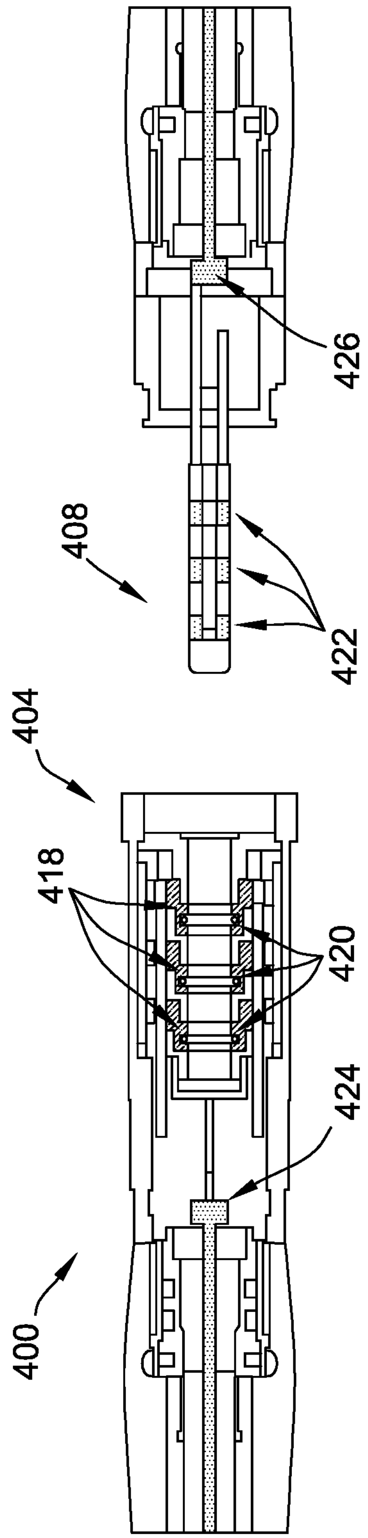
Figure 4C:
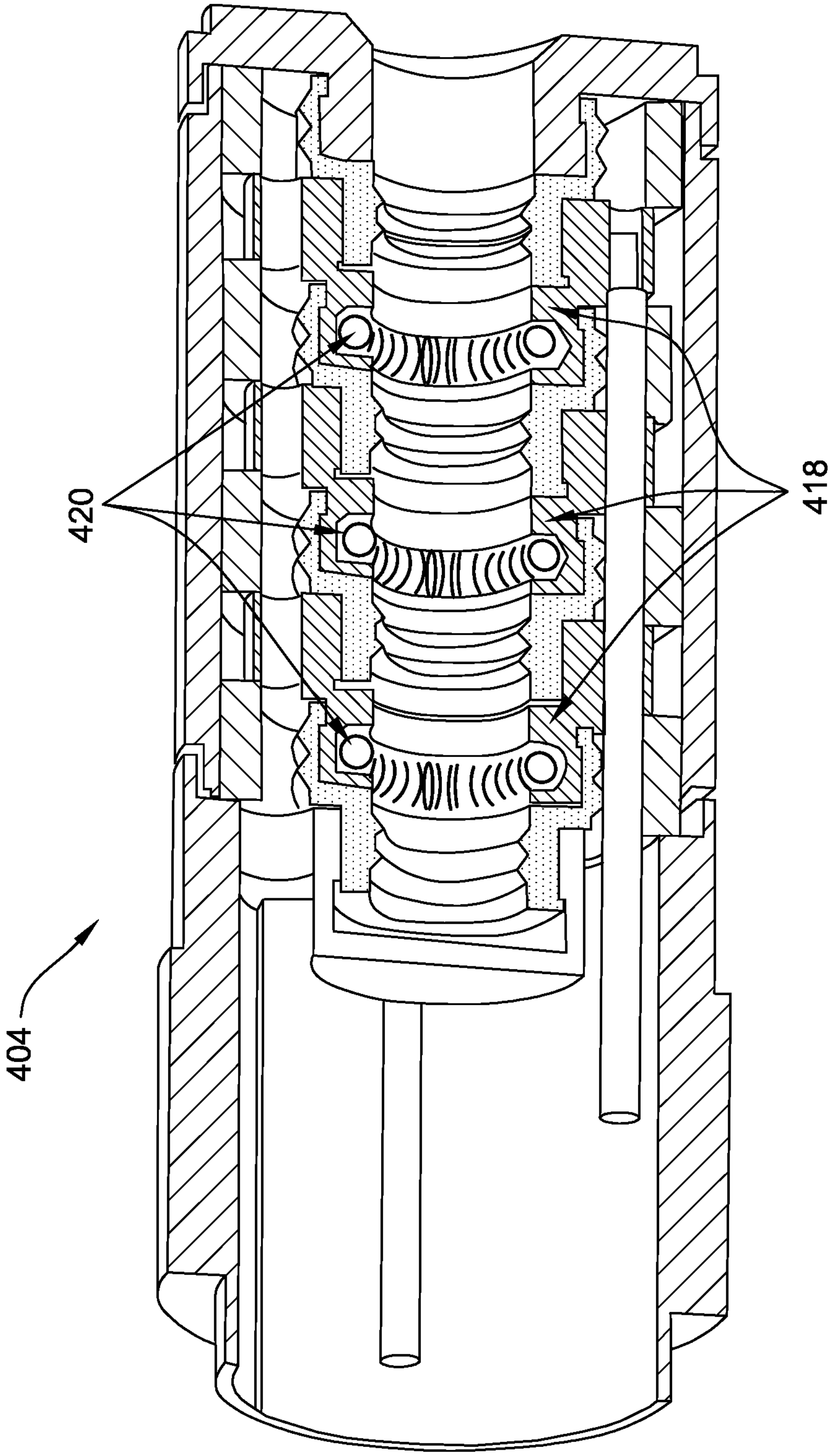

FIG. 4B shows a cutaway view of connector assembly 400 shown in FIG. 4A. Female connector 404 may include one or more o-rings 418 disposed within a jack of female connector 404 that either surround or are positioned on both sides of female electrical contacts 420 also disposed within the jack of female connector 404. In some embodiments, other fluid-sealing mechanisms may be employed in lieu of, or in addition to, o-rings 418. O-rings 418 surrounding female electrical contacts 420 may be implemented as wiper seals, as shown in FIG. 4C below. Female electrical contacts 420 and o-rings 418 are configured to form an interference fit with male electrical contacts 422 on the plug of male connector 408 when male connector 408 is inserted into female connector 404.

O-rings 418 acting as wiper seals are configured to perform two functions: they "wipe" male connector 408 of fluid, debris, and/or bodily fluids during insertion, and also electrically isolate the electrical connection between female electrical contacts 420 and male electrical contacts 422 when male connector 408 is fully inserted into female connector 404. Female connector 404 may include an electrical interface 424, such as electrical interface 310 (shown in FIG. 3). Male connector 408 may include an electrical interface 426, such as electrical interface 318 (shown in FIG. 3). Electrical interfaces 424 and 426 may carry power and control signals through female connector 404 and male connector 408, respectively.

O-rings 418 acting as wiper seals may include an electrically isolating material designed to isolate female electrical contacts 420 of female connector 404. The wiper seals may be configured to scrape, wipe, or remove fluid or other debris from male connector 408 as it is inserted into female connector 404. Those of skill in the art will appreciate from the foregoing that o-rings 418 isolate individual female electrical contacts 420 from one another. In this manner, a secure and isolated connection is formed with each contact.

FIG. 4C shows an enlarged view of o-rings 418 and female electrical contacts 420 of female connector 404. Female electrical contacts 420 may include a leaf spring and/or a wire mesh (as described in further detail below), which allows for movement of female electrical contacts 420 as they engage their corresponding male electrical contacts 422 (shown in FIG. 4B). As shown, female connector 404 may include three female electrical contacts 420 configured to couple to three male electrical contacts 422 when male connector 408 (show in FIG. 4B) is inserted into female connector 404.

In one embodiment, female electrical contacts 420 may include platinum iridium alloy (Pt—Ir). Platinum iridium has a high corrosion resistance. This is particularly important for implanted devices because, in the example embodiment, connector assembly 400 (shown in FIGS. 4A and 4B) is saturated in blood and bodily fluids when disconnected inside the body. Although Pt—Ir exemplifies excellent corrosion resistance, its mechanical properties and poor manufacturability may make it unsuitable for connector applications. Accordingly, conventional medical devices typically use other materials, which are easier to manufacture. For example, pacemakers typically use MP35N for connectors, which may be resistance welded to a wire. These materials are sufficient when exposed to most bodily fluids but have insufficient resistance when saturated in blood for long periods. These materials typically will corrode and fail when exposed to continuous voltages from a high voltage implanted medical device.

Accordingly, pacemakers are typically placed subcutaneously in a pacemaker pocket in the upper torso in part to limit exposure to stresses and strains. The pacemaker location is also relatively easy to access for component replacement. In contrast, connector assembly 400 may be placed deep in the abdominal area where connector assembly 400 is exposed to high pull forces and stresses. This application is far more demanding than typical medical applications. In addition to the anatomical differences, the high power run through the example connector assembly 400 (e.g., several watts or more of continuous power) further increases the risk of corrosion compared to conventional devices, such as pacemaker leads.

Figure 5A:
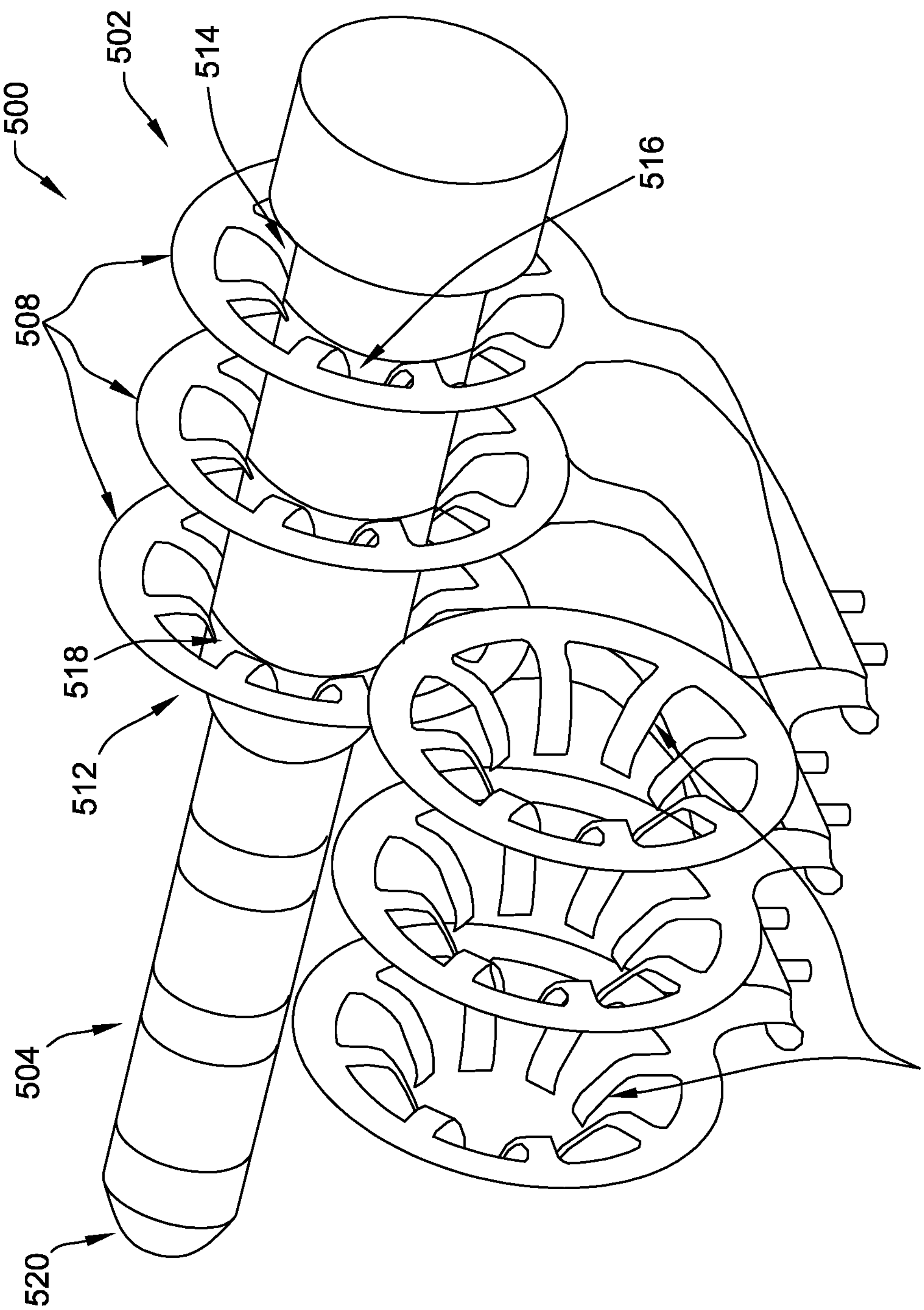
FIGS. 5A-5F illustrate various embodiments of female electrical contact assemblies that may be used with the electrical connector shown in FIGS. 4A-4C.

FIG. 5A shows one embodiment of a connector assembly 500, such as connector assembly 400 (shown in FIGS. 4A and 4B). Connector assembly 500 includes a female connector 502, such as female connector 404 (shown in FIGS. 4A-4C) and a male connector 504, such as male connector 408 (shown in FIGS. 4A and 4B). Female connector 502 includes a plurality of female electrical contacts 508, such as female electrical contacts 420 (shown in FIGS. 4B and 4C). Each female electrical contact 508 includes a plurality of leaf springs 510 manufactured from a single sheet of material (not shown). For example, the manufacturing leaf springs 510 may include (a) die cutting the sheet of material by shearing the sheet of material with dies and (b) forming, using the same die or a different die, the sheet of material into a particular shape (e.g., the shape of leaf springs 510) by plastically deforming the one sheet of material. By manufacturing leaf springs 510 from one sheet of material, leaf springs 510 are interconnected with each other as they are formed using the same sheet of material. This results in female electrical contacts 508 formed in one piece. By using one sheet of material to form leaf springs 510, the amount of material that is not used (i.e., wasted) to form leaf springs 510 is significantly reduced, thereby requiring less amount of material compared to methods that require multiple sheets to form leaf springs 510.

In the example embodiment, each female electrical contact 508 includes an outer ring 512, and leaf springs 510 extend inward from outer ring 512. Each leaf spring 510 forms a curved blade 514 configured to contact male electrical contacts 516, such as male electrical contacts 422 (shown in FIG. 4B). In particular, each curved blade 514 includes an end tip 518 that contacts one of male electrical contacts 516. End tip 518 may be rectangular or circular, for example, and may extend towards an end 520 of male connector 504. The cross section of end tip 518 may be rectangular or circular, for example.

In the example embodiment, each curved blade 514 extends both radially inward from outer ring 512 and longitudinally towards end 520, such that each curved blade 514 may contact a corresponding male electrical contact 516 when male connector 504 is inserted into female connection 502. By extending curved blades 514 both radially inward and longitudinally towards end 520, the friction between curved blades 514 and male electrical contacts 516 may be reduced while the amount of contact between curved blades 514 and male electrical contacts 516 may be increased.

Additionally, leaf springs 510 provide at least one of the following advantages: (i) reduction of manufacturing processes required to electrically and/or mechanically join components by combining leaf springs 510 with curved blades 514, and by producing multiple leaf springs 510 per part that may be separated at a later date (e.g., similar to how molds may produce more than one part per shot); (ii) creation of a hermetic receptacle stack, without including the opening of the receptacle, as there is an amount of radial surface area of outer ring 512 that enables creating a hermetic braze with ceramic insulators when male connector 504 is inserted into female connector 502; and (iii) increase of high applied pressure resistance because outer ring 512 has a relatively small external surface area. This increase of resistance is particularly important during the manufacturing process, when considering the potential for direct overmolding of the receptacle stack at pressures typical for injection molding of implantable materials, as these pressures may be relatively high. For example, thermoplastic polyurethane (TPU) (e.g., the material used for encapsulating electrical headers throughout implantable devices, such as cardiac rhythm management (CRM) and neuro devices) is molded at approximately 10,000 psi. The wall thickness required to resist this pressure is very high, which leads to very costly use of precious alloys used, such as Pt, Pd, and the like. The example embodiment shown in FIG. 5A does not require a thick wall as ceramic bushings (e.g., a fixture) may be added between each leaf spring 510, enabling leaf springs 510 to be held under high compression with the fixture during overmolding, where the ceramic may be bonded to leaf springs 510 with or without chemically bonding.

Figure 5B:
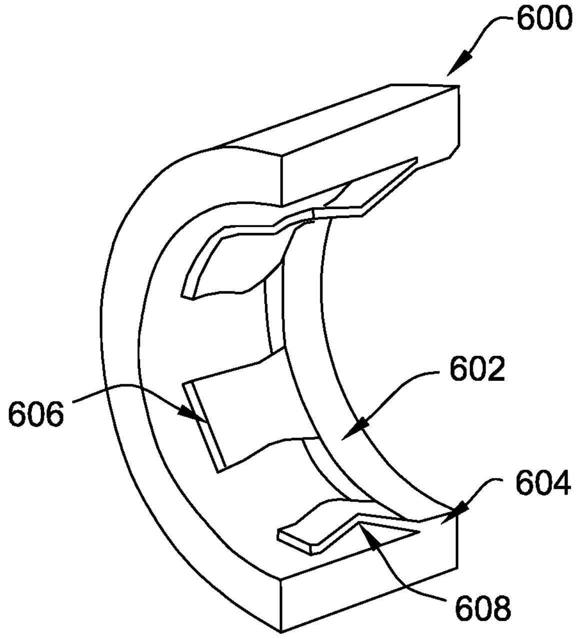

FIG. 5B shows a perspective cross-sectional view of an alternative female electrical contact 600 that includes a plurality of leaf springs 602 coupled to a tube 604. Leaf springs 602 may be manufactured from a single sheet of material (not shown), and the manufacturing process of leaf springs 602 may be similar to that described in reference to FIG. 5A. Each leaf spring 602 forms a curved blade 606 configured to contact male electrical contacts (not shown). Leaf springs 602 extend generally longitudinally along tube 604 (e.g., in a generally cylindrical shape), and include an indent 608 that projects radially inward. Leaf springs 602 are configured such that indents 608 are biased to press against the male electrical contacts.

Figure 5C:
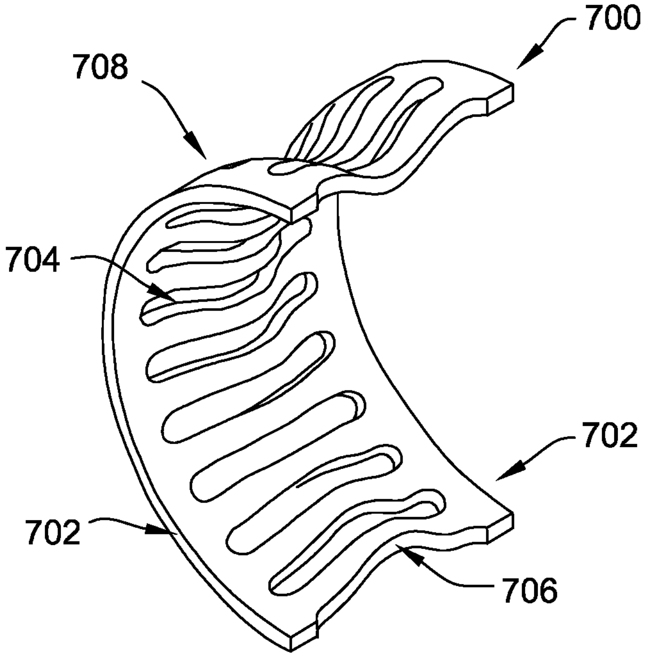

FIG. 5C shows a perspective cross-sectional view of an alternative female electrical contact 700. Female electrical contact 700 includes two circumferentially extending rails 702, and a plurality of ribs 704 extending between rails 702 and configured to contact male electrical contacts (not shown). Each rib 704 has an indent 706 that extends radially inward, and each rib 704 is configured such that indents 706 are biased to press against male electrical contacts. In this embodiment, each rib 704 extends generally longitudinally. Female electrical contact 700 may be manufactured, for example, by stamping a sheet of material (not shown) that is then formed into a cylinder or a tube 708. In an alternative embodiment, female electrical contact 700 may be manufactured by cutting a tube (not shown) that is then formed into shape of tube 708 to avoid a seam between ends of sheet folded into tube 708. In another embodiment, the seam between the ends of sheet is welded together. Tube 708 may be formed using seamless tubing manufacturing or welded tubing manufacturing practices.

Figure 5D:
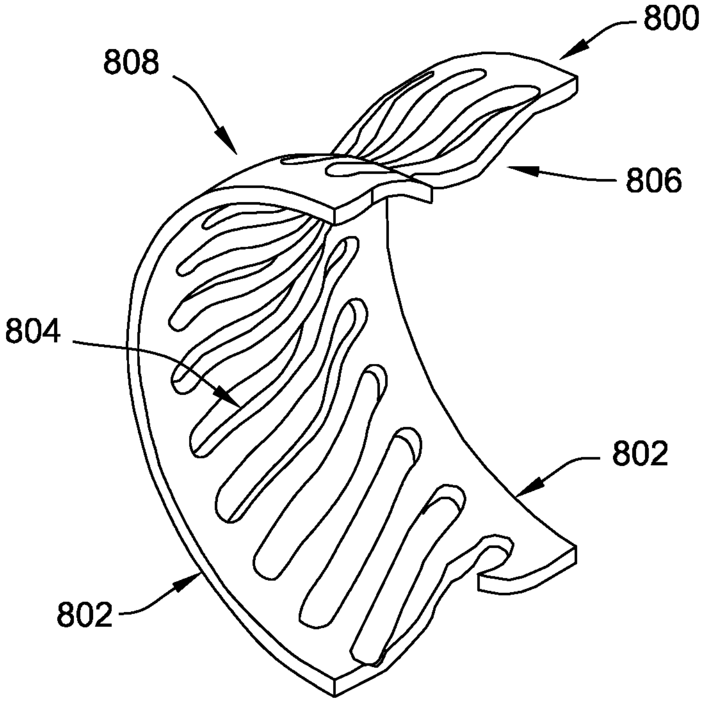

FIG. 5D shows a perspective cross-sectional view of an alternative female electrical contact 800. Female electrical contact 800 includes two circumferentially extending rails 802, and a plurality of ribs 804 extending between rails 802 and configured to contact male electrical contacts (not shown). Each rib 804 has an indent 806 that extends radially inward, and each rib 804 is configured such that indents 806 are biased to press against male electrical contacts. In this embodiment, each rib 804 extends generally at an oblique angle with respect to rails 802. Female electrical contact 800 may be manufactured by stamping a sheet of material (not shown) that is then formed into a cylinder or tube 808. In an alternative embodiment, female electrical contact 800 may be manufactured by cutting a tube (not shown) that is then formed into shape of tube 808 to avoid a seam between ends of sheet folded into tube 808. In another embodiment, the seam between the ends of sheet is welded together. Tube 808 may be formed using seamless tubing manufacturing or welded tubing manufacturing practices.

Figure 5E:
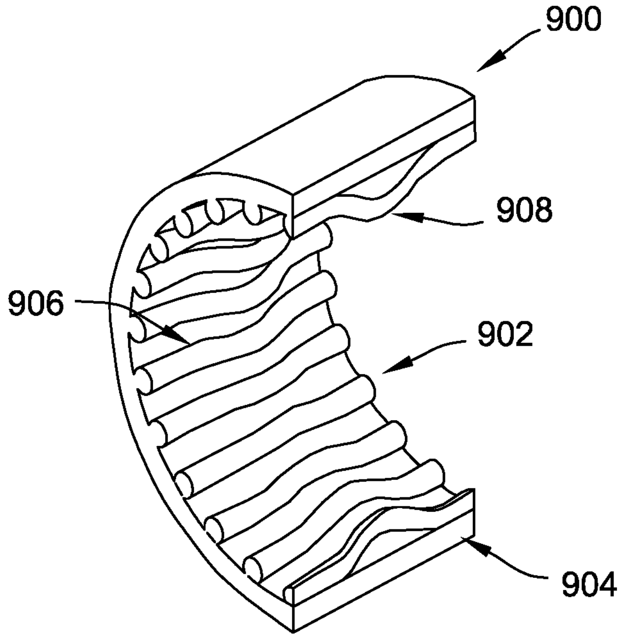

FIG. 5E shows a perspective cross-sectional view of an alternative female electrical contact 900. Female electrical contact 900 includes a wire mesh 902, similar to a stent, coupled to a tube 904. Wire mesh 902 includes a plurality of wires 906 extending generally longitudinally along tube 904 and configured to contact male electrical contacts (not shown). Each wire 906 has an indent 908 that extends radially inward, and each wire 906 is configured such that indents 908 are biased to press against male electrical contacts. In this embodiment, each wire 906 has a cylindrical cross-section. In other embodiments, each wire 906 may have any suitable shape. Female electrical contact 900 may be manufactured by stamping a sheet of material (not shown) that is then formed into a cylinder or tube 904. In an alternative embodiment, female electrical contact 900 may be manufactured by cutting a tube (not shown) that is then formed into shape of tube 904 to avoid a seam between ends of sheet folded into tube 904. In another embodiment, the seam between the ends of sheet is welded together. Tube 904 may be formed using seamless tubing manufacturing or welded tubing manufacturing practices.

Figure 5F:
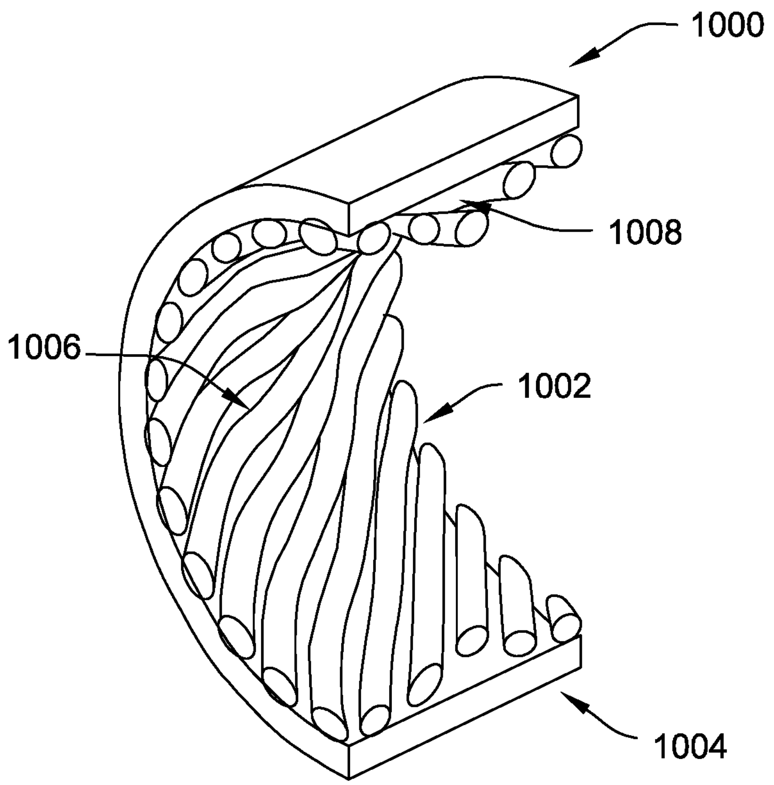

FIG. 5F shows a perspective cross-sectional view of an alternative female electrical contact 1000. Female electrical contact 1000 includes a wire mesh 1002, similar to a stent, coupled to a tube 1004. Wire mesh 1002 includes a plurality of wires 1006 extending generally at an oblique angle along tube 1004 and configured to contact male electrical contacts (not shown). Each wire 1006 has an indent 1008 that extends radially inward, and each wire 1006 is configured such that indents 1008 are biased to press against male electrical contacts. In this embodiment, each wire 1006 has a cylindrical cross-section. In other embodiments, each wire 1006 may have any suitable shape. Female electrical contact 1000 may be manufactured by stamping a sheet of material (not shown) that is then formed into a cylinder or tube 1004. In an alternative embodiment, female electrical contact 1000 may be manufactured by cutting a tube (not shown) that is then formed into shape of tube 1004 to avoid a seam between ends of sheet folded into tube 1004. In another embodiment, the seam between the ends of sheet is welded together. Tube 1004 may be formed using seamless tubing manufacturing or welded tubing manufacturing practices.

The embodiments described herein provide systems and methods for connections in a medical device system. Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A connector assembly for use in a medical device system, the connector assembly configured to communicate power and control signals to a medical device, the connector assembly comprising:

a female connector comprising:

a jack; and at least one female electrical contact disposed in the jack, the at least one female electrical contact comprising a wire mesh coupled to a tube, the wire mesh including a plurality of wires each extending longitudinally along the tube;

a male connector comprising:

a plug adapted to be inserted into the jack of the female connector, and at least one male electrical contact disposed on the plug, the at least one male electrical contact configured to electrically couple to a corresponding female electrical contact of the at least one female electrical contact by contacting the plurality of wires of the corresponding female electrical contact when the plug of the male connector is inserted into the jack of the female connector.

2. The connector assembly of claim 1, wherein each wire of the plurality of wires comprises an indent extending radially inward and configured to contact the at least one male electrical contact.

3. The connector assembly of claim 1, wherein each wire of the plurality of wires has a cylindrical cross-section.

4. The connector assembly of claim 1, wherein the at least one female electrical contact comprises platinum iridium.

5. The connector assembly of claim 1, wherein the medical device system is one of a wirelessly powered implantable system and a wired powered implantable system.

* * * * *